US012186261B2

(12) United States Patent
Yan et al.

(10) Patent No.: US 12,186,261 B2
(45) Date of Patent: Jan. 7, 2025

(54) ION PULSE TREATMENT APPARATUS FOR EYES

(71) Applicant: SPINEYE HEALTH TECHNOLOGY CO., LTD, Shanghai (CN)

(72) Inventors: Shihong Yan, TaiYuan (CN); Kaili Gu, Shanghai (CN)

(*) Notice: Subject to any disclaimer, the term of this patent is extended or adjusted under 35 U.S.C. 154(b) by 1219 days.

(21) Appl. No.: 16/960,533

(22) PCT Filed: Dec. 29, 2018

(86) PCT No.: PCT/CN2018/125891
§ 371 (c)(1),
(2) Date: Jul. 7, 2020

(87) PCT Pub. No.: WO2019/137269
PCT Pub. Date: Jul. 18, 2019

(65) Prior Publication Data
US 2021/0059901 A1 Mar. 4, 2021

(30) Foreign Application Priority Data
Jan. 11, 2018 (CN) .......................... 201810027773.7

(51) Int. Cl.
*A61H 39/00* (2006.01)
*A61N 1/04* (2006.01)
*A61N 1/36* (2006.01)

(52) U.S. Cl.
CPC ......... *A61H 39/002* (2013.01); *A61N 1/0484* (2013.01); *A61N 1/36014* (2013.01); *A61H 2201/165* (2013.01); *A61H 2205/024* (2013.01)

(58) Field of Classification Search
CPC .... A61H 23/0263; A61H 39/002; A61H 5/00; A61H 2201/1207; A61H 2201/165;
(Continued)

(56) References Cited

U.S. PATENT DOCUMENTS 5,360,438 A * 11/1994 Fisher ................ A61N 1/36031
607/141
2010/0296977 A1* 11/2010 Hancock ................... A61L 2/24
422/186
(Continued)

FOREIGN PATENT DOCUMENTS

CN 1072081 A * 5/1993
CN 101352389 A * 1/2009
(Continued)

*Primary Examiner* — Justine R Yu
*Assistant Examiner* — Matthew R Moon
(74) *Attorney, Agent, or Firm* — Tsz Lung Yeung

(57) ABSTRACT

The present invention discloses an ion pulse treatment apparatus for eye, which includes a carrier for carrying conductor elements to the eye acupoint regions; a power supply provided on the carrier and electrically connected to a control board; a high voltage generating element on the carrier and electrically connected to the control board; and two conductor elements carried by the carrier and used for treatment, wherein the two conductor elements are provided to contact with the surface skin of the eye acupoint regions, wherein one conductor element of the two conductor elements is electrically connected to a ground terminal of the high voltage generating element, and the other conductor element is electrically connected to a high voltage terminal of the high voltage generating element, wherein the negative ions (electrons) generated by the ion pulse treatment apparatus for eye of the present invention have the function of promoting microcirculation in the eye regions after entering the eye acupoint regions, so as to accelerate cell metabolism, effectively relieve eye fatigue, and promote eye health.

7 Claims, 11 Drawing Sheets

(58) Field of Classification Search
CPC ...... A61H 2201/5097; A61H 2205/024; A61N 1/0404; A61N 1/36014; A61N 1/36046; A61N 1/44
See application file for complete search history.

(56) References Cited

U.S. PATENT DOCUMENTS

| | | | |
|---|---|---|---|
| 2016/0051439 A1* | 2/2016 | Brown | A61H 23/0245 601/46 |
| 2019/0099606 A1* | 4/2019 | Shah | A61N 1/08 |

FOREIGN PATENT DOCUMENTS

| | | | | |
|---|---|---|---|---|
| CN | 202230263 U | * | 5/2012 | |
| CN | 107049312 A | * | 8/2017 | ............. A61B 5/398 |
| CN | 206526247 U | * | 9/2017 | ............... A61H 5/00 |
| DE | 102010027201 A1 | * | 7/2011 | ........... A61N 1/0404 |
| WO | WO-2017152790 A1 | * | 9/2017 | |

* cited by examiner

ION PULSE TREATMENT APPARATUS FOR EYES

CROSS REFERENCE OF RELATED APPLICATION

This application claims the benefit under 35 U.S.C. § 119 from International Application No. PCT/CN 2018/125891, which claims priority to CN 201810027773.7, filed Jan. 11, 2018.

BACKGROUND OF THE PRESENT INVENTION

Field of Invention

The present invention relates to an ion pulse treatment apparatus for eye, which is adapted for relieving eye fatigue.

Description of Related Arts

As we all know, too long use of eyes is easy to cause visual fatigue, and too long use of eyes in short distance is easy to cause ciliary muscle fatigue. In order to alleviate eye fatigue, the existing solutions are mainly as follows:

1. Based on far-infrared technology: for example, an eyeglass frame having physiotherapy function with the application No. 201510679807.7, which includes a lens frame and a lens foot; two sides of the lens frame are connected with the lens foot, which further includes a physiotherapy device arranged on an inner side of the lens foot; wherein the physiotherapy device is consist of a shell, an infrared light, a circuit board, a USB interface and a switch; wherein several infrared lights are stuck in an inner side wall of the shell, the circuit board is provided inside the shell, the USB interface and the switch are provided at an outer side wall of the shell and the USB interface, the switch and the infrared lights are connected to the circuit board. When wearing glasses, turn on the switch, activate the infrared lights, and perform infrared physiotherapy on the corners of the wearer's eyes, to relieve the pressure on the eyes caused by long-term wear.

2. Energy magnet technology: for example, a titanium magnet anti-fatigue eye protection glasses with the application No. 201710516588. X, which includes two left and right frames, temples connected to the left and right frames and nose pads, wherein an upper side of each frame is provided with three titanium magnets, a lower side of each frame is provided with one titanium magnet. The titanium magnets embedded in glasses can release negative oxygen ions and far-infrared rays, reduce visual fatigue, block electromagnetic radiation, keep brain clear, relieve eye fatigue, relax ciliary muscle, prevent electromagnetic radiation and solve the problem of eye fatigue.

3. Massage techniques, such as common eye exercises.

In practice, the existing technical solutions are still unsatisfactory in terms of alleviating human eye fatigue and in view of this, the inventor abandons the existing technology and re-develops a better human eye fatigue relief product, which is different from the existing technology in principle and technical scheme.

SUMMARY OF THE PRESENT INVENTION

The object of the present invention is to provide an ion pulse treatment apparatus for eye to solve the above problems, which can relieve eye fatigue.

In order to solve the above technical problems, the present invention provides an ion pulse treatment apparatus for eye, which includes a carrier for carrying conductor elements to the eye acupoint regions; a power supply provided on the carrier and electrically connected to a control board; a high voltage generating element on the carrier and electrically connected to the control board; and two conductor elements carried by the carrier and used for treatment, wherein the two conductor elements are provided to contact with the surface skin of the eye acupoint regions, wherein one conductor element of the two conductor elements is electrically connected to a ground terminal of the high voltage generating element, and the other conductor element is electrically connected to a high voltage terminal of the high voltage generating element.

Compared with the prior art, the negative ions (electrons) of the ion pulse treatment apparatus for eye of the present invention has the function of promoting the microcirculation of the eye area after entering the eye acupoint region, so as to accelerate cell metabolism, effectively relieve the eye fatigue, and promote eye health.

In the ion pulse treatment apparatus for eye of the present invention, the conductor elements are electrical conductors and/or semi-conductors. The conductors include but are not limited to metals, graphite and some metal compounds (such as WC). The metals include silver, copper, aluminum, tungsten, iron, manganese copper alloy, nickel aluminum alloy, nickel chromium alloy, etc. The semi-conductors include but are not limited to elemental semiconductors (Ge, Si, Se, etc.), inorganic compound semiconductors (ZnSiP2, SiC, and Ge—Si alloy, etc.), organic compound semiconductors (naphthalene, anthracene, polyacrylonitrile, phthalocyanine, etc.).

In the ion pulse treatment apparatus for eye of the present invention, the eye acupoint regions may be contacted by the two conductor elements, which include: Zanzhu acupoint, Jingming acupoint, Yuyao acupoint, Sizhukong acupoint, Tongziliao acupoint, Chengqi acupoint, Taiyang acupoint, Yangbai acupoint and Sibai acupoint.

Jingming acupoint, as mentioned above, is located at the inner side of the eye and in the concave slightly above the inner corner of the eye (on the human face, the concave above the inner canthus angle of the eye).

Zanzhu acupoint, as mentioned above, is located on the human face, at the depression of the head of the eyebrow and the frontal notch.

Taiyang acupoint, as mentioned above, is located at the side of the head, and it lays at a depression a horizontal finger back away from the middle of the brow tip and the outer corner of the eye.

Tongziliao acupoint, as mentioned above, is located at a depression 0.5 cun away from the outer side of the outer canthus of the face.

Yuyao acupoint, as mentioned above, is located at the forehead, directly/right above the pupil and in the eyebrow.

Sizhukong acupoint, as mentioned above, is located at a depression of the brow tip of the face.

Chengqi acupoint, as mentioned above, is located directly/right below the pupil when the eyes look straight ahead, and it is located at the lower edge of the orbit, where the eyeball is in contact with the orbit.

Yangbai acupoint, as mentioned above, is located at the forehead, directly/right above the pupil and the position 1 cun away from eyebrow.

The above eye acupoint regions usually are massaged (such as eye health exercise), while the product provided by the present invention can make eye treatment and eye fatigue alleviation more targeted.

In the ion pulse treatment apparatus for eye of the present invention, a high voltage output terminal of the high voltage generating element provided at the carrier is connected with a vacuum discharge tube or an ion efficiency intensifier, for example, the ion efficiency intensifier can adopt the relevant patent product applied by the present company.

In the ion pulse treatment apparatus for eye of the present invention, the carrier may be a head wearable device and/or a face wearable device.

In the ion pulse treatment apparatus for eye of the present invention, when the carrier is a head wearable device, it may be a sport headband, a hat or a helmet.

In the ion pulse treatment apparatus for eye of the present invention, when the carrier is a wearable device, the face wearable device is a spectacle frame, a mask or a blinder.

In the ion pulse treatment apparatus for eye of the present invention, the carrier is provided with a concealed wiring channel or a concealed wiring groove.

In the ion pulse treatment apparatus for eye of the present invention, two conductor elements carried by the carrier are installed on the carrier body in a detachable manner.

In the ion pulse treatment apparatus for eye of the present invention, when the carrier is a face wearable device, the face wearable device is provided with a counterweight.

In the ion pulse treatment apparatus for eye of the present invention, when the carrier is a spectacle frame of the face wearable device, a corner position-limit mechanism is arranged between the spectacle temple and the lens frame of the spectacle frame.

In the ion pulse treatment apparatus for eye of the present invention, the two conductor elements are respectively provided at two nose pads of the spectacle frame, wherein the two conductor elements are electrical conductors and/or semi-conductors. The conductors include but are not limited to metals, graphite and some metal compounds (such as WC). The metals include silver, copper, aluminum, tungsten, iron, manganese copper alloy, nickel aluminum alloy, nickel chromium alloy, etc. The semi-conductors include but are not limited to elemental semiconductors (Ge, Si, Se, etc.), inorganic compound semiconductors (ZnSiP2, SiC, and Ge—Si alloy, etc.), organic compound semiconductors (naphthalene, anthracene, polyacrylonitrile, phthalocyanine, etc.).

In the ion pulse treatment apparatus for eye of the present invention, the control board is provided with a wireless communication module.

In the ion pulse treatment apparatus for eye of the present invention, the carrier is provided with a far-infrared device or an energy magnet.

DETAILED DESCRIPTION OF THE PREFERRED EMBODIMENT

Figure 1:
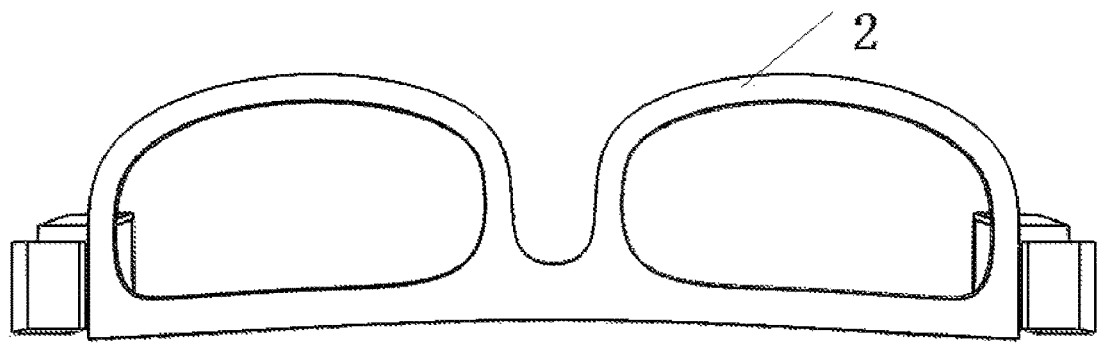
FIG. 1 is a front view of an ion pulse treatment apparatus for eye according to a first embodiment of the present invention.
Figure 2:
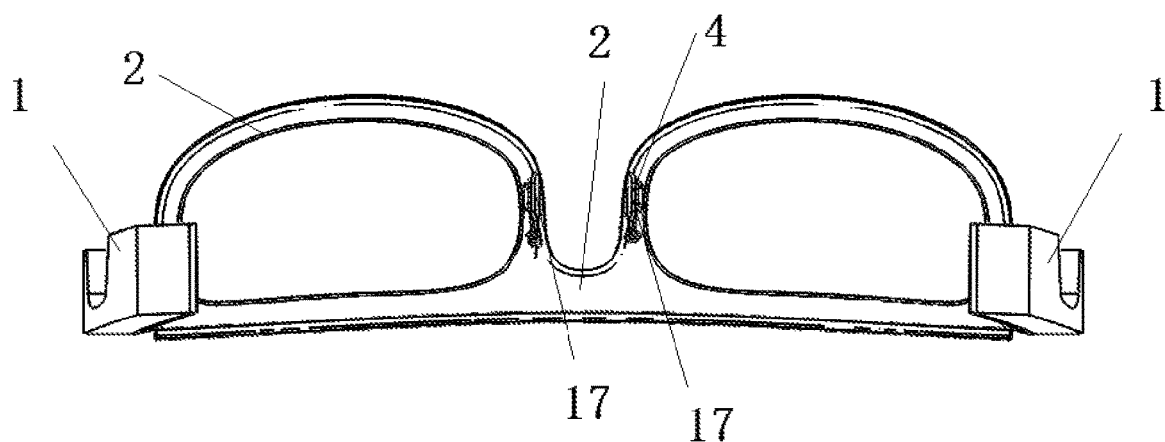
FIG. 2 is a rear view of the ion pulse treatment apparatus for eye according to the above first embodiment of the present invention.
Figure 3:
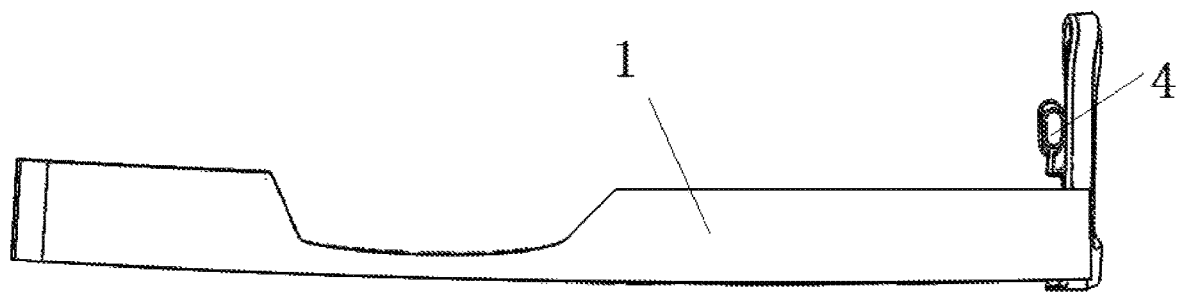
FIG. 3 is a left view of the ion pulse treatment apparatus for eye according to the above first embodiment of the present invention.
Figure 4:
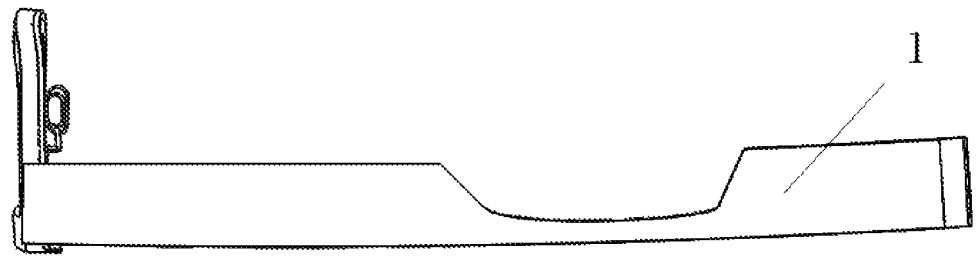
FIG. 4 is a right view of the ion pulse treatment apparatus for eye according to the above first embodiment of the present invention.
Figure 5:
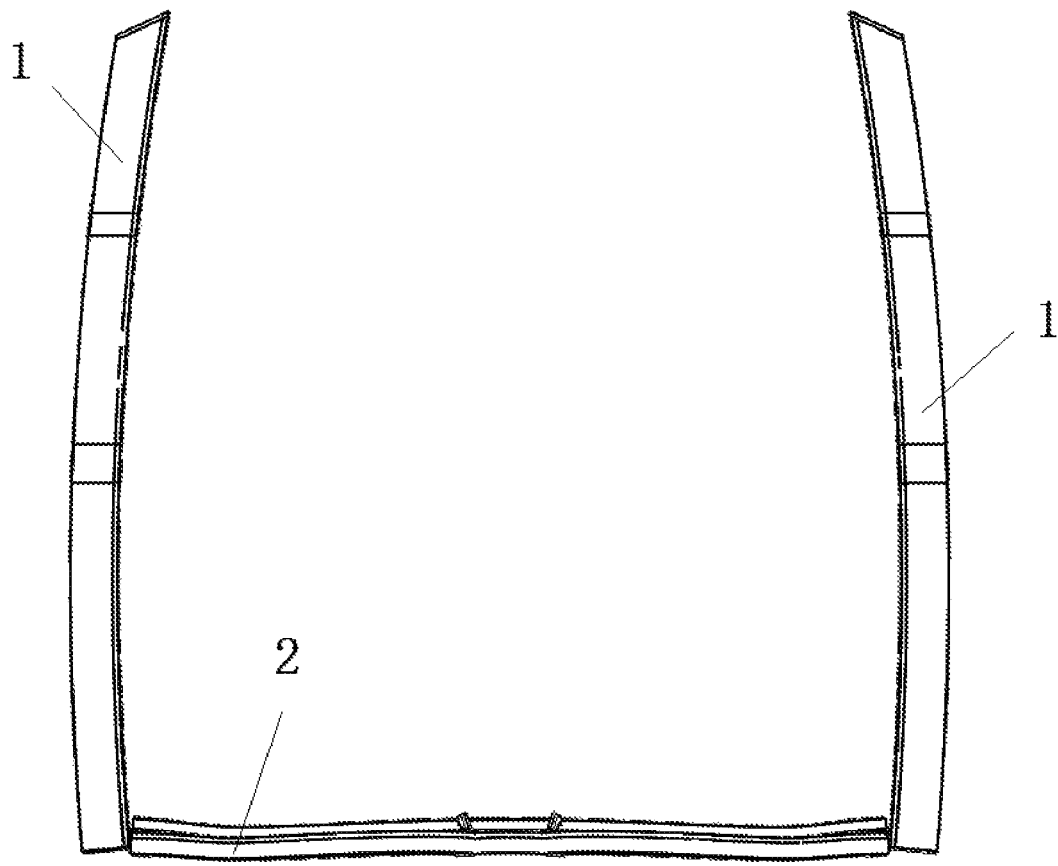
FIG. 5 is a top view of the ion pulse treatment apparatus for eye according to the above first embodiment of the present invention.
Figure 6:
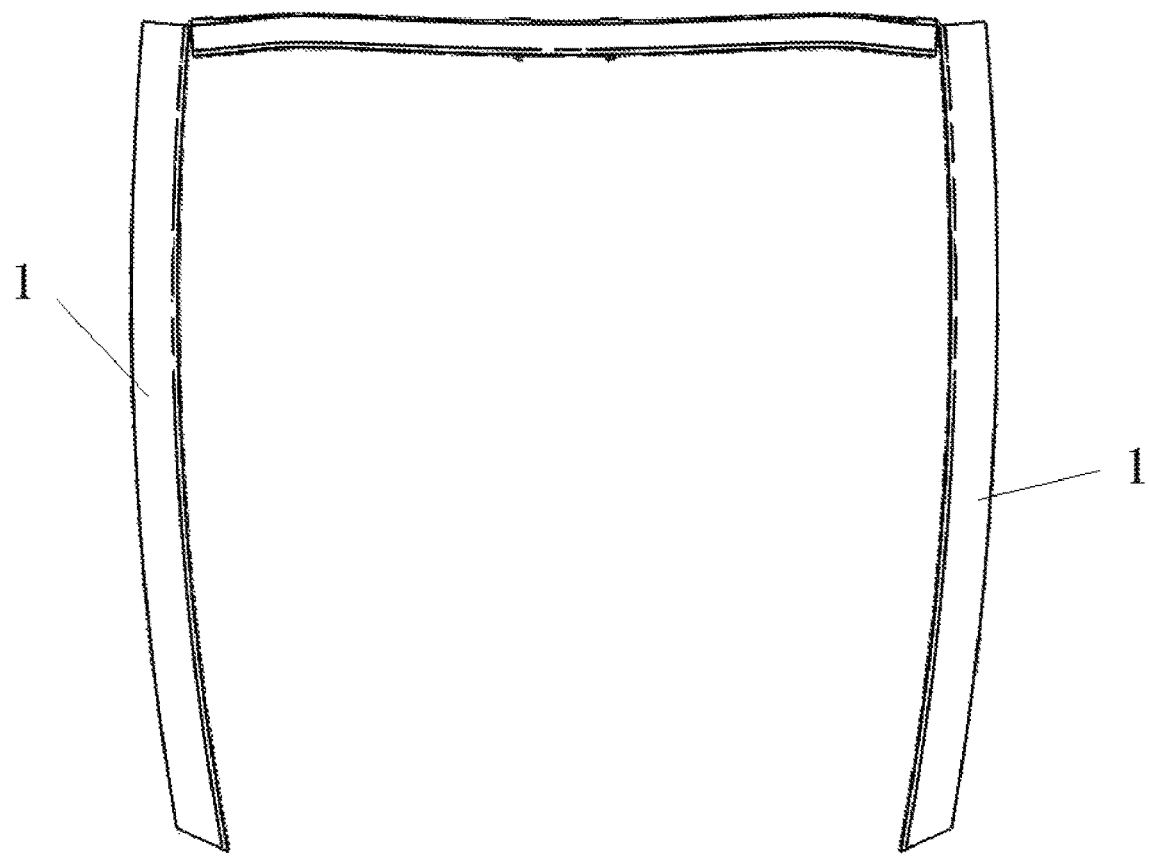
FIG. 6 is a bottom view of the ion pulse treatment apparatus for eye according to the above first embodiment of the present invention.

In order to easily understand the technical means implementing the present invention, creative features, achieved goals and effects, the present invention will be further illustrated in conjunction with specific embodiments as below.

A first embodiment of the present invention provides an ion pulse treatment apparatus for eye, which comprises: a carrier, used for carrying conductor elements 17 to the eye acupoint regions, wherein the carrier is illustrated by taking a spectacle frame selected from face wearable devices as an example. Referring to FIGS. 1 to 7, the spectacle frame which is configured as the carrier, comprises two spectacle temples 1, a lens frame 2, a nose bridge (middle beam) 3 connecting two ring-shaped spectacle rings of the lens frame 2 together, and nose pads 4 disposed on the spectacle rings of the lens frame 2, wherein the installation of lenses is not necessary, whether to or not install the lenses can be selected according to the demand.

The spectacle frame is provided with a power supply 14, which is electrically connected to a control board 16, and the power supply 14 can be, for example, a battery. And a high voltage generating element 15 disposed on the spectacle frame, is electrically connected to the control board 16. Two conductor elements 17 carried at the nose pads 4 of the spectacle frame and used for treatment, can be in contact with the surface skin of the eye acupoint regions, wherein one conductor element of the two conductor elements 17 is electrically connected to a ground terminal of the high voltage generating element 15, and the other conductor element is electrically connected to a high voltage terminal of the high voltage generating element 15. Except the two conductor elements 17 are exposed, the power supply 14, the high voltage generating element 15 and the control board 16 of the ion pulse treatment apparatus for eye can be exposed, or can be concealed inside the spectacle frame. That is to say, the spectacle frame is configured with a concealed wiring channel or a concealed wiring groove. If the power supply 14, the high voltage generating element 15 and the control board 16 are exposed, the spectacle frame, the power supply 14, the high voltage generating element 15 and the control board 16 can be assembled at the spectacle frame by adopting a certain connection types such as snap connection, screw fixing, magnetic adsorption etc.

Figure 8:
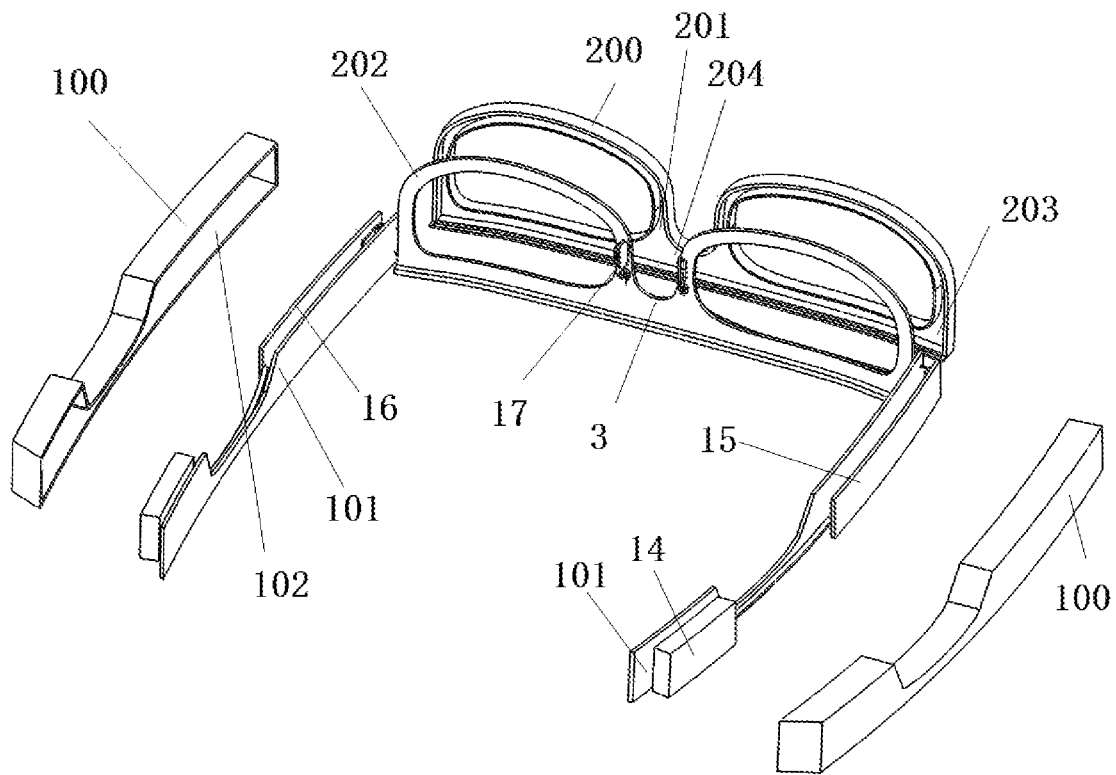
FIG. 8 is an exploded view of the ion pulse treatment apparatus for eye according to the above first embodiment of the present invention.

Referring to FIG. 8, the spectacle temple 1 of the spectacle frame can be divided into a temple outer frame 100 and a temple cover 101 mounted on an opening side of the temple outer frame 100, wherein the temple outer frame 100 has a concealed wiring groove 102, if the temple cover 101 is not mounted, a side opening of the concealed wiring groove 102 is exposed, however, when the temple cover 101 is mounted on the temple outer frame 100, the concealed wiring groove 102 is covered by the temple cover 101, thereby forming a concealed wiring channel in the spectacle temple 1, so that it is clear that the concealed wiring channel can be defined when a cover plate is disposed on the side opening of the concealed wiring groove 102. And the temple cover 101 can be detachably mounted on the temple outer frame 100 by screws. In the same way, the lens frame 2 can be divided into a lens frame body 200 with a route groove 201 and a lens frame cover 202 corresponding to the lens frame body 200, wherein the lens frame cover 202 can be mounted on a side opening of the lens frame body 200. The spectacle temples 1 can be respectively and rotatably mounted on the lens frame 2 through a rotation shaft, for example, the spectacle temples 1 can be respectively and rotatably mounted on the lens frame cover 202. And the lens frame cover 202 can be detachably mounted on the lens frame body 200 by bolting. It is worth noting that the route groove of the lens frame body 200 comprises two circumferential grooves 203 surrounding the two spectacle rings of the lens frame 2, and a nose bridge groove 204 provided at the nose bridge (middle beam) 3 and communicating with the two circumferential grooves 203 respectively. After the lens frame body 200 is closed by the lens frame cover 202, the concealed wiring channel of the lens frame 2 is defined.

As shown in FIG. 8, the installation structures of the power supply 14, the high voltage generating element 15 and the control board 16 on the spectacle frame are illustrated, as described below. The battery 14 and the high voltage generating element 15 are mounted within the temple outer frame 100 of one spectacle temple 1, wherein the high voltage generating element 15 can be, for example, a high voltage plate. The high voltage generating element 15 may also be other high voltage generating devices, such as a piezoelectric high voltage generating device or a coil high voltage generating device. The control board 16 is mounted within the temple outer frame 100 of the other spectacle temple 1, and the wirings between the elements are arranged in the concealed wiring channels of the lens frame 2 and the spectacle temple 1. And the two conductor elements 17 mounted at the nose pads 4 define a first conductor and a second conductor respectively, wherein the first conductor is mounted on one nose pad 4, and the second conductor is mounted on the other nose pad 4. The two conductor elements 17 include, but are not limited to plates, blocks, and spheres, as long as they are in surface contact or point contact with the human skin surface. The material of the conductor elements 17 may be selected from conductive materials, including but not limited to conductive silica gel, conductive metal sheet, carbon fiber material, and the material of the conductor elements 17 may also be a semi-conductive material (semiconductor material). And the conductor elements 17 can be embedded in the original nose pads 4 of the spectacle frame for mounting, or the conductor elements 17 can be directly made into a nose pad structure and mounted on the spectacle frame. Here, the conductor elements 17 are directly made into the nose pads 4 and mounted on the spectacle frame, and the conductor elements 17 are electrical conductors and/or semi-conductors, that is, the nose pads 4 can be electrical conductors, may also be semi-conductors, or can be made of a mixed material of electrical conductor material and semi-conductor material.

Figure 9:
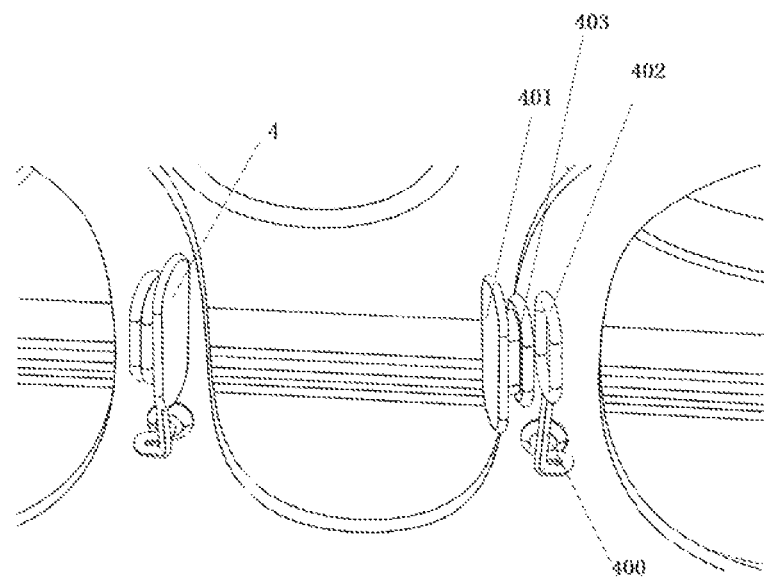
FIG. 9 is a partial schematic view of the nose pads in the ion pulse treatment apparatus for eye according to the above first embodiment of the present invention.

As a further improvement to the first embodiment, the two conductor elements (electrodes) 17 carried by the carrier configured by the spectacle frame are detachably mounted on the carrier, wherein the detachable structures of the conductor elements 17 include, but are not limited to: magnetic adsorption connection mechanism, mechanical snap-slot connection mechanism, snap connection mechanism, and screw fixed connection mechanism. Referring to FIG. 9, take the snap connection mechanism as an example, the nose pad 4 comprises a nose arm 400 as a supporting leaf holder, a supporting leaf 401 mounted on the nose arm 400, wherein both of the nose arm 400 and the supporting leaf 401 are made of conductive material, wherein the nose arm 400 is provided with a snap ring 402, and the supporting leaf 401 has a snap connector 403 matched with the snap ring 402, an end of the snap connector 403 is provided with a flexible flange, and the other end of the snap connector 403 connected with the body of the supporting leaf 401, wherein the flexible flange includes but is not limited to rubber. And the nose arm 400 is connected to the high voltage plate through wires. The snap connector 403 and the snap ring 402 fit tightly with each other. In FIG. 9, the left nose pad 4 is mounted in position, while the right nose pad 4 is in a separated state, so as to enable a person of ordinary skill in the art to clearly understand the detachable structure of the nose pad 4. Since the conductor elements 17 define the supporting leafs 401, the supporting leafs 401 and the conductor elements 17 actually belong to one same structure. An existing spectacle frame is provided with the nose pads 4 omitting the nose arms 400, so the sheet or blocky electrodes are detachably mounted at the nose pads 4, for example, a magnetic adsorption base can be disposed at the nose pad 4 to magnetically adsorb the electrodes on the magnetic adsorption base. It is also possible to provide an electrode slice mounting groove at the nose pad 4 to embed the electrodes in the groove, or to provide a snap holder at the nose pad 4 to snap the electrodes at the snap holder.

Figure 12:
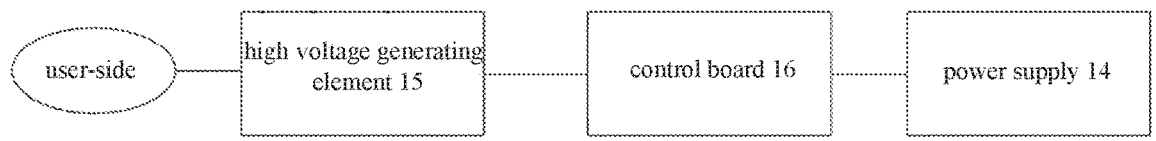
FIG. 12 is a block diagram of the circuit principle of the ion pulse treatment apparatus for eye according to the above first embodiment of the present invention.

Referring to FIG. 12, which shows the original circuit of the ion pulse treatment apparatus for eye, wherein the power supply 14 is used as a power supply element of the entire apparatus to perform power-supplying operation, and the control board 16 controls the high voltage generating element 15, and the user-side connected to the high voltage generating element 15 is the two conductor elements 17.

Figure 10:
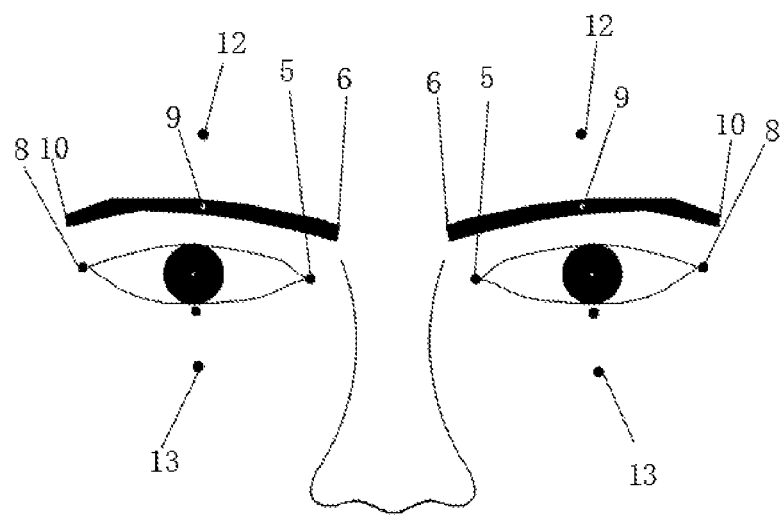
FIG. 10 is a distribution diagram of the acupoints in the eye acupoint regions according to the above first embodiment of the present invention.
Figure 11:
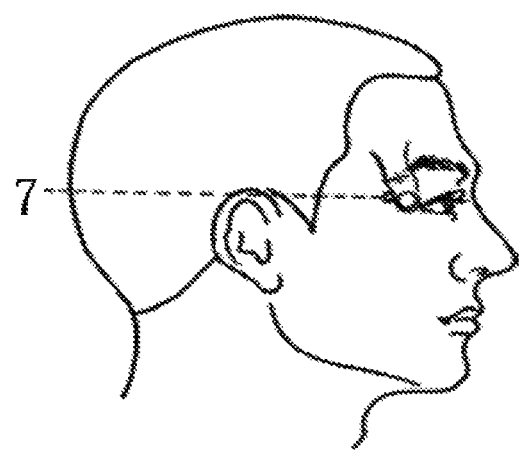
FIG. 11 is a schematic diagram of the position of Taiyang acupoint in the eye acupoint regions according to the above first embodiment of the present invention.

The ion pulse treatment apparatus for eye provided by the present invention can choose to mount the two conductor elements 17 at a corresponding position according to a chosen eye acupoint region to be stimulated. FIG. 10 shows the corresponding positions of the eye acupoints, wherein each Jingming acupoint 5 is located at the inner side of the eye and in the concave slightly above the inner corner of the eye (on the human face, the concave above the inner canthus angle of the eye); each Zanzhu acupoint 6 is located on the human face, at the depression of the head of the eyebrow and the frontal notch; each Tongziliao acupoint is located at a depression 0.5 cun away from the outer side of the outer canthus of the face; each Yuyao acupoint 9 is located at the forehead, directly/right above the pupil and in the eyebrow; each Sizhukong acupoint 10 is located at a depression of the brow tip of the face (FIG. 10 shows the position of the acupoint from the side); each Chengqi acupoint 11 is located directly/right below the pupil when the eyes look straight ahead, and it is located at the lower edge of the orbit, where the eyeball is in contact with the orbit; each Yangbai acupoint 12 is located at the forehead, directly/right above the pupil and the position 1 cun away from eyebrow; each Sibai acupoint 13 is located 1 cun below the eye, at the position under the infraorbital foramen, directly facing the pupil of the eye. Referring to FIG. 11, each Taiyang acupoint 7 is located at the side of the head, and it lies in a depression a horizontal finger back away from the middle of the brow tip and the outer corner of the eye. The above eye acupoint regions usually are massaged (such as eye health exercise) or other technical means to relieve fatigue, while the product provided by the present invention can make eye treatment and eye fatigue alleviation more be targeted.

The ion pulse treatment apparatus for eye shown in FIGS. 1 to 7, can act on the Jingming acupoint. Since the nose pads 4 are arranged symmetrically, the two conductor elements 17 are arranged symmetrically. If need to stimulate the acupoints at other positions of the eye, fixing the conductor elements 17 on the spectacle frame to correspond to the corresponding acupoints, for example, if need to stimulate the Taiyang acupoint, fixing one of the conductor elements 17 on the left spectacle temple 1 and fixing the other conductor element 17 on the right spectacle temple 1. The contact between the conductor element 17 and the surface skin of the acupoint may be point contact, or surface contact.

As can be seen from the above, the negative ions (electrons) of the ion pulse treatment apparatus for eye provided by the present invention have the function of promoting microcirculation in the eye regions after entering the eye acupoint regions, so that cell metabolism is accelerated, eye fatigue is effectively relieved, and eye health is promoted.

Figure 13:
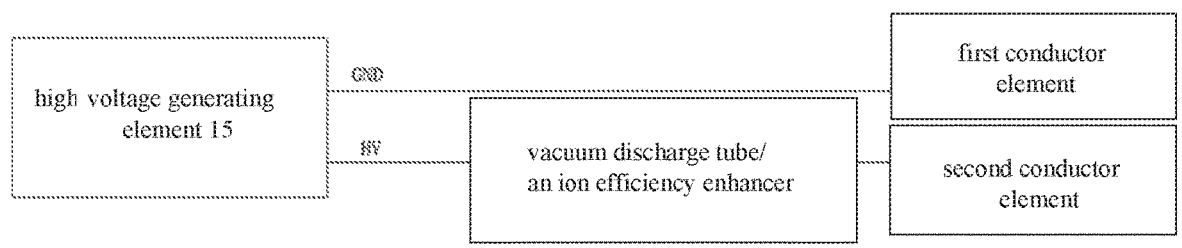
FIG. 13 is a schematic diagram of the connection between a vacuum discharge tube or an ion efficiency intensifier and a high voltage generating element.

Referring to FIG. 13, as a further improvement to the first embodiment, a high voltage output terminal of the high voltage generating element 15 on the carrier is connected with a vacuum discharge tube or ion efficiency intensifier, after adding the element such as the vacuum discharge tube or ion efficiency intensifier, the penetration effect of reduced ions can be enhanced. It should be noted that the first conductor element and the second conductor element of the two conductor elements 17 shown in FIG. 11, that is, the two conductor elements 17 mentioned above, are respectively mounted at the two nose pads 4.

Figure 15:
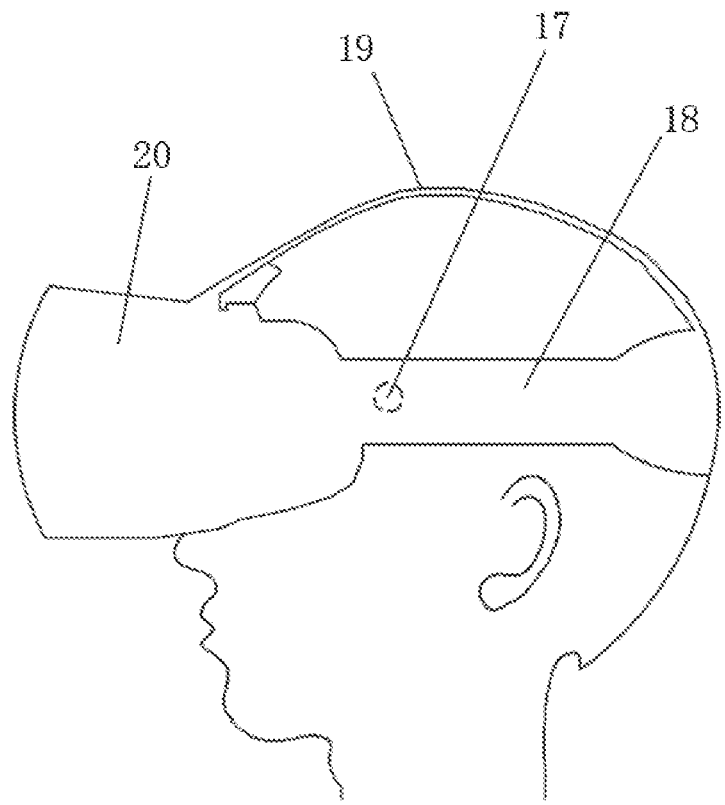
FIG. 15 is a schematic diagram of an ion pulse treatment apparatus for eye according to a second embodiment of the present invention.

A second embodiment of the present invention provides an ion pulse treatment apparatus for eye, which comprises: a carrier, used for carrying the conductor elements 17 to the eye acupoint regions, wherein the carrier is illustrated by taking a wearable helmet selected from head wearable devices as an example, referring to FIG. 15. The wearable helmet is provided with the conductor elements 17 near the Taiyang acupoint of the human body, wherein the conductor elements 17 are selected as disc-shaped metal conductors.

The simplified wearable helmet only comprises a surrounding fixing portion 18 for surrounding the head and an overhead surrounding portion 19, one end portion of the overhead surrounding portion 19 is fixed to the surrounding fixing portion 18 at the back side of head, and the other end portion is fixed to the surrounding fixing portion 18 near the forehead, and the surrounding fixing portion 18 can be provided with a mounting block 20 for the power supply 14, the high voltage generating element 15 and the control board 16 at the position of the eye.

Of course, in order to stimulate other acupoint regions of the eye, the conductor elements 17 can be mounted at the corresponding position of the mounting block 20 to match the corresponding acupoints.

Figure 16:
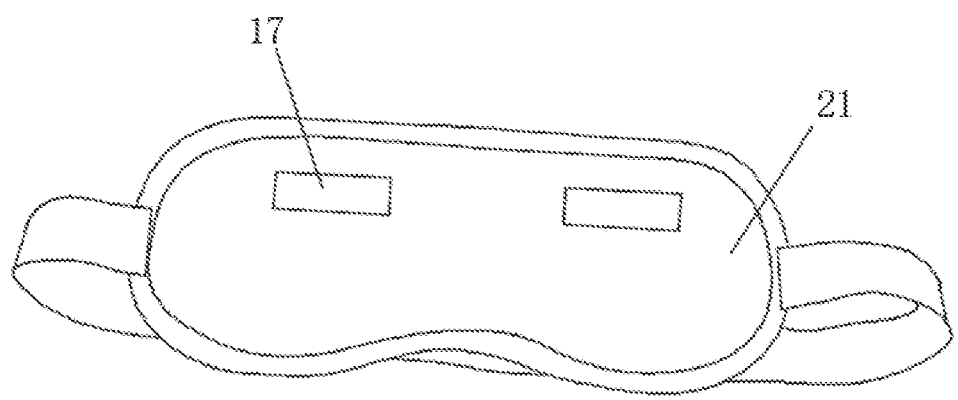
FIG. 16 is a schematic diagram of an ion pulse treatment apparatus for eye according to a third embodiment of the present invention.

A third embodiment of the present invention provides an ion pulse treatment apparatus for eye, which comprises: a carrier, used for carrying the conductor elements 17 to the eye acupoint regions, wherein taking a blinder selected from face wearable devices as an example for description. Referring to FIG. 16, the blinder 21 is provided with the conductor elements 17 near the Yangbai acupoint 12 of the human body, wherein the conductor elements 17 are selected as rectangular metal plates (such as iron plate, copper plate, silver plate, etc.).

The power supply 14, the high voltage generating element 15 and the control board 16 are placed within the blinder 21, wherein when the blinder 21 is made of two layers of fabric, the sandwiched space between the two layers of fabric defines a accommodating space for the power supply 14, the high voltage generating element 15 and the control board 16, the concealed wiring channel defined from the route channel defined by stitching the two layers of fabric is for receiving the wires. For the convenience of fixing, a plurality of accommodating bags for each element can be provided in the interlayer, and the power supply 14, the high voltage generating element 15 and the control board 16 can be placed in respective accommodating bags, wherein the openings of the accommodating bags can be stitched, or in a non-stitched state. When the strap of the blinder 21 wears the blinder 21 on the eye, the rectangular metal plates are just in contact with the Yangbai acupoints 12. Since there is a Yangbai acupoint 12 above each of the left eye and the right eye, the two rectangular metal plates respectively correspond to the Yangbai acupoints 12 where they are located.

As can be seen from the third embodiment, if necessary, the area of the metal plate can be increased to cover multiple acupoints at the same time, such as covering the Zanzhu acupoint 6, the Yuyao acupoint 9, the Sizhukong acupoint 10, and the Yangbai acupoint 12 at the same time. As for the metal plate, a convex column facing the corresponding acupoint may be provided on the surface of the metal plate for easy replacement of the contact acupoint, for example, a convex portion facing the Yuyao acupoint 9 is disposed so as to better contact with the Yuyao acupoint 9.

As can be seen from the above embodiments, for the carrier, the head wearable device and the face wearable device can also be in other forms, for example, the head wearable device can also be sport headband, hat or helmet, etc., the face wearable device can also be a mask. Regardless of the wearable devices, if the covering surface of the existing product cannot cover the eye acupoint regions, by extending the wearable device to the eye acupoint regions to cover the eye acupoint regions. Taking the mask as an example, if the mask cannot cover the upper area of the eye, at this time, by extending the upper edge of the mask toward the forehead of the human body to cover the Yangbai acupoint region, and the conductor elements 17 can be mounted in the area where the mask covers the Yangbai acupoint.

Figure 7:
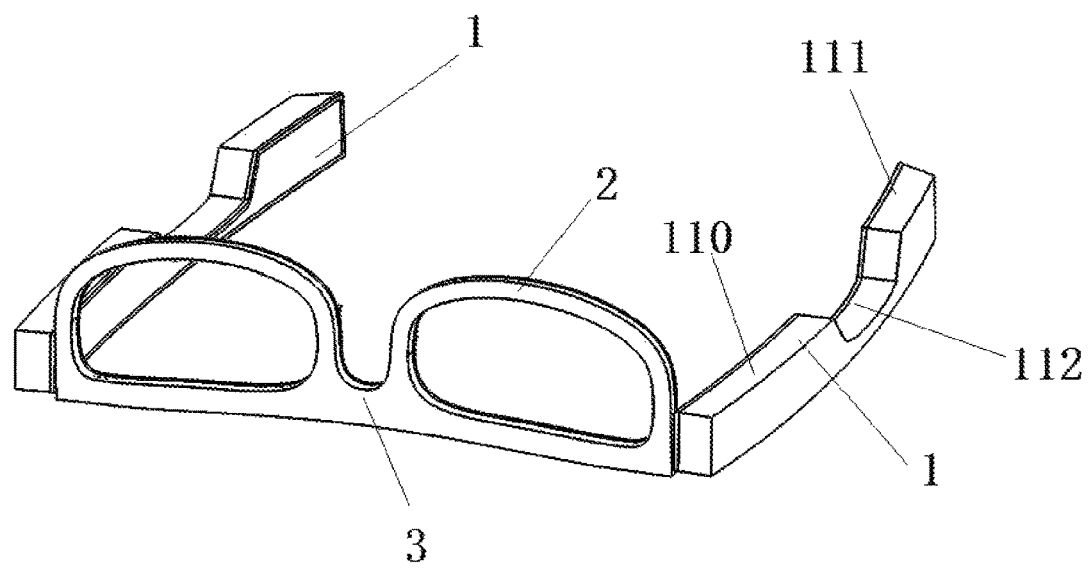
FIG. 7 is a perspective view of the ion pulse treatment apparatus for eye according to the above first embodiment of the present invention.
Figure 14:
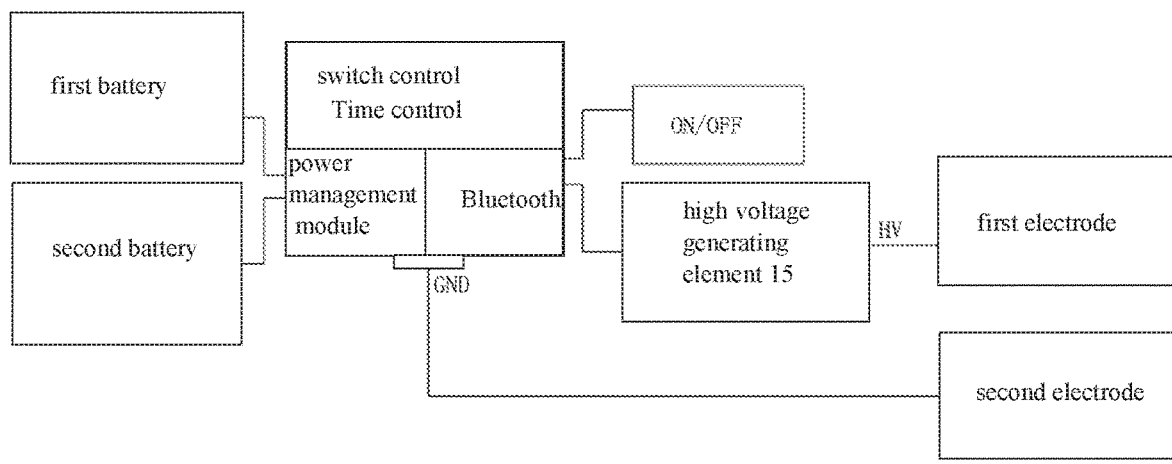
FIG. 14 is a schematic diagram of the circuit of the ion pulse treatment apparatus for eye according to the above first embodiment of the present invention.

In addition, referring to FIG. 7, the spectacle temple 1 has an ear front portion 110 adapted to be located in front of the ear and an ear rear portion 111 adapted to be located behind the ear, wherein the ear front portion 110 of the spectacle temple 1 is connected to the lens frame 2, the adjacent position of the ear front portion 110 and the ear rear portion 111 of the spectacle temple 1 is an ear support portion 112, the ear support portion 112 is a recess provided between the ear front portion 110 and the ear rear portion 111, a counterweight is mounted at the ear rear portion 111, wherein the counterweight may be a metal block or other heavy objects with a certain quality. As an option, the counterweight can be placed inside the ear rear portion 111 of the spectacle temple 1, comparing with the external counterweight, the whole structure is more convenient to use. When the counterweight is configured as a built-in structure, the ear rear portion 111 is provided with a counterweight accommodation cavity (counterweight installation position, counterweight placement position), the counterweight accommodation cavity is provided with an opening, and the opening is provided with a cover plate. Referring to FIG. 8, the counterweight accommodation cavity is a part of the inner cavity of the spectacle temple 1, wherein the spectacle temple 1 has the temple outer frame 100, and the temple cover 101 is disposed at an opening side of the temple outer frame 100, wherein the temple cover 101 is detachably mounted on the temple outer frame 100, for example, the temple cover 101 is mounted on the temple outer frame 100 by screws. As can be seen from FIG. 8, the counterweight is the power supply battery 14 of the ion pulse treatment apparatus for eye, and the power supply 14 for the entire ion pulse treatment apparatus for eye is two batteries respectively arranged in the counterweight placement position provided in the two spectacle temples 1, the two batteries 14 are communicated in parallel with each other to power the entire ion pulse treatment apparatus for eye. Referring to FIG. 14, the two batteries 14 respectively define a first battery and a second battery (such as a 250 mAh lithium battery), wherein the first battery and the second battery are communicated in parallel with each other and connected to a power management module of the control board 16, and the control board 16 is provided with a Bluetooth module, a switch control, a time control module, and the control board 16 is provided with an ON/OFF interface, wherein the ON/OFF interface can adopt mechanical buttons, or be wirelessly connected to an external control device through the Bluetooth module, such as controlled by a remote control or a mobile device (such as a mobile phone) equipped with a control APP. After the two batteries are communicated in parallel and connected to the power management module, the charging function can be realized, of course, a USB charging port may also be provided at the power management module to achieve charging, and a first electrode and a second electrode are mounted at the carrier (the first conductor and the second conductor in FIG. 13 can be replaced by the first electrode and the second electrode here). It should be noted that the temple outer frame 100 and the temple cover 101 are provided with recess portions matching with each other at the ear support portion 112, so as to form the ear support portion 112 of the spectacle temple 1 after assembled. Since the battery is mounted at the ear rear portion 111, during the use of consumers, the human ear serves as a fulcrum, and the battery can form a lever effect, so that the weight pressed against the nose pads 4 is dispersed by the battery, thereby reducing the possibility of uncomfortable symptoms after the body surface is pressed by the nose pads 4 for a long time. When the carrier is a face wearable device, the face wearable device is provided with a counterweight, which can effectively reduce the weight pressing against the surface of the human body from the conductor elements 17. The above describes the counterweight of the spectacle frame, the human ear can also serve as the fulcrum, arranging a counterweight rod at the ear rear portion 111, and an ear front part of the counterweight rod is connected to the face wearable devices, when the carrier is the other face wearable device. Taking the mask as an example, two ear front parts of the two counterweight rods can be respectively fixed to the left and right edges of the mask, so that the mask can be lifted upwards, thereby reducing the pressure on the face, which comes from the elements placed inside the mask.

In addition, the control board 16 can be provided with a wireless communication module such as a Bluetooth module, a LIFI module, a WIFI module, a 3G module, and a 4G module, etc., so that the external control device can send control instructions to the control board 16.

As an option, the carrier is provided with far infrared devices or energy magnets. Taking the spectacle frame as an example, the far infrared devices or the energy magnets can be mounted on the lens frame 2. If it is the other carrier, such as a helmet, the far infrared devices or the energy magnets can be arranged on the structure which covers the eye acupoint regions.

A fourth embodiment of the present invention provides an ion pulse treatment apparatus for eye, wherein the structure of the apparatus can refer to the first embodiment, the second embodiment, and the third embodiment, the difference is that the fourth embodiment provides a negative ion generating circuit adapted for the above embodiments, which comprises, a CPU module, a boost module, a high voltage module, a power supply unit, wherein the power supply unit comprises a charging module, a charger connected to the charging module, and a battery connected to the charging module. The power supply unit is connected to the CPU module and the boost module, the CPU module is connected to the boost module, the booster module is connected to the high voltage module. One electrode of the two electrodes in contact with the human body is connected to the high voltage module, and the other electrode is grounded. The two electrodes in contact with the human body are arranged at the nose pads 4 of the spectacle frame and fixed at the nose pads 4 of the spectacle frame by adhesion or snapping.

Figure 17:
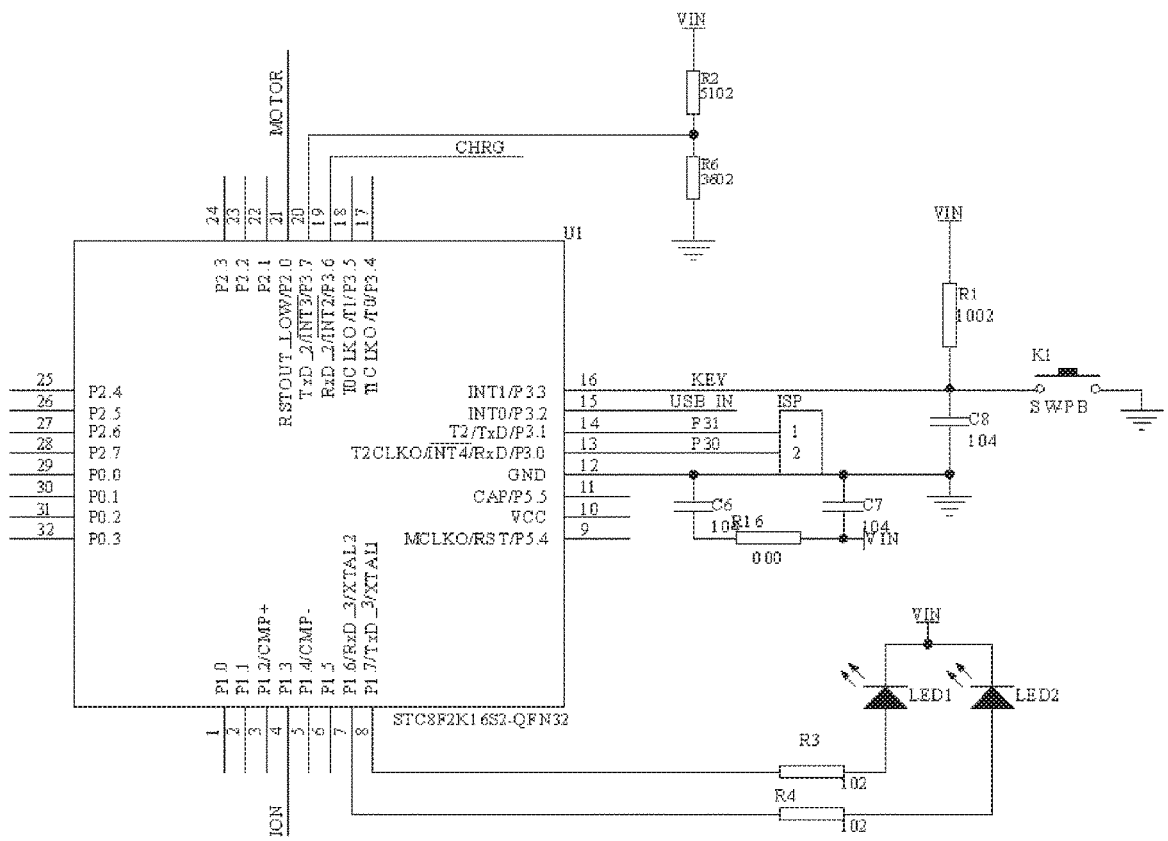
FIG. 17 is a circuit schematic diagram of a CPU module in a negative ion generating circuit of an ion pulse treatment apparatus for eye according to a fourth embodiment of the present invention.

Referring to FIG. 17, the CPU module employs the STC8F2K16S2-QFN32 chip. FIG. 17 shows the CPU module and a supporting peripheral circuit thereof, wherein the CPU module comprises a control chip U1, wherein a pin 1, a pin 2, a pin 3, a pin 5, a pin 6, a pin 9, a pin 10, a pin 11, a pin 17, a pin 18, a pin 22, a pin 23, pins 24-32 of the control chip U1 are empty pins. A pin 4 of the control chip U1 is connected to the boost module, a pin 7 of the control chip U1 is connected to a resistor R4, wherein the resistor R4 is connected to one light emitting diode LED2, a pin 8 of the control chip U1 is connected to another light emitting diode LED1 through a resistor R3, wherein the light emitting diode LED2 and the light emitting diode LED1 are connected to a power input terminal VIN, wherein a pin 12 of the control chip U1 is connected with a capacitor C6 and a capacitor C7, a resistor R16 is connected between the capacitor C6 and the capacitor C7, wherein the resistor R16 and the capacitor C7 are connected to the power input terminal VIN, and the pin 12 of the control chip U1 is also connected to a capacitor C8, one end of the capacitor C8 is grounded, another end is connected to the power input terminal VIN through a resistor R1. The pin 13 and the pin 14 of the control chip U1 are connected to the ISP (pins for downloading the program), the pin 15 of the control chip U1 is connected to the charging module, a pin 16 of the control chip U1 is connected between the capacitor C8 and the resistor R1, and the pin 16 of the control chip U1 is grounded through a control switch K1 (SW-PB, the power switch of the spectacle frame), the pin 19 of the control chip U1 is connected to the charging module, the pin 20 of the control chip U1 is connected between a resistor R2 and a resistor R6, the resistor R6 is grounded, and the resistor R2 is connected to the power input terminal VIN.

Figure 18:
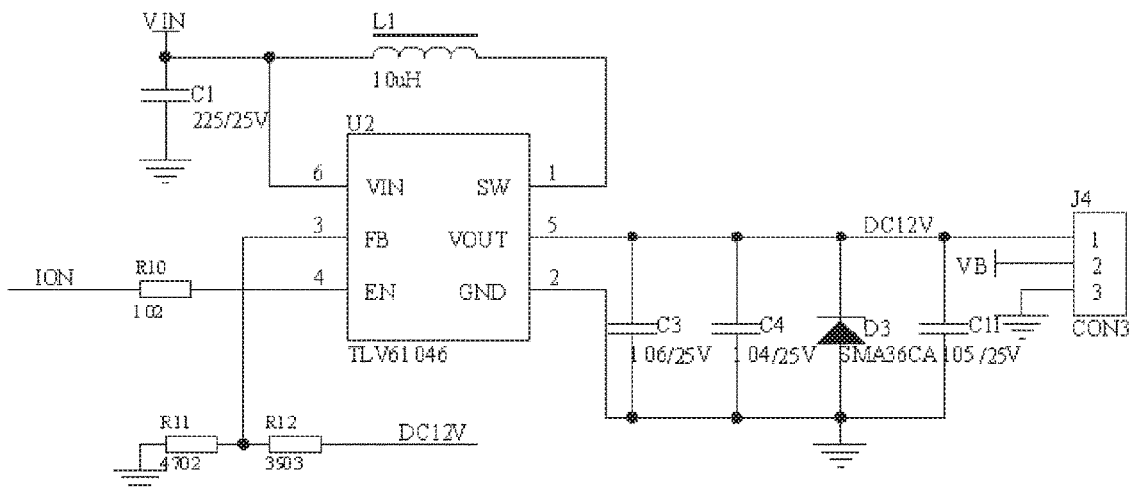
FIG. 18 is a circuit schematic diagram of a booster module in the negative ion generating circuit of the ion pulse treatment apparatus for eye according to the above fourth embodiment of the present invention.

Referring to FIG. 18, the booster module comprises: a control chip U2, such as TLV61046 chip, a pin 1 of the control chip U2 is connected to the power input terminal VIN through an inductor L1, a capacitor C3, a capacitor C4, a diode D3, and a capacitor C11 are provided between a pin 2 and a pin 5 of the control chip U2, the pin 2 of the control chip U2 is grounded, the pin 5 of the control chip U2 is connected to a connector J4, a pin 2 of the connector J4 is connected to the high voltage module, a pin 4 of the control chip U2 is connected to the CPU module through a resistor R10, a pin 3 of the control chip U2 is connected with a resistor R11 and a resistor R12, one end of the resistor R11 is grounded, the resistor R12 is connected to DC12V power supply 14, that is, a VOUT terminal of the booster chip, a pin 6 of the control chip U2 is connected to the power input terminal VIN.

Figure 19:
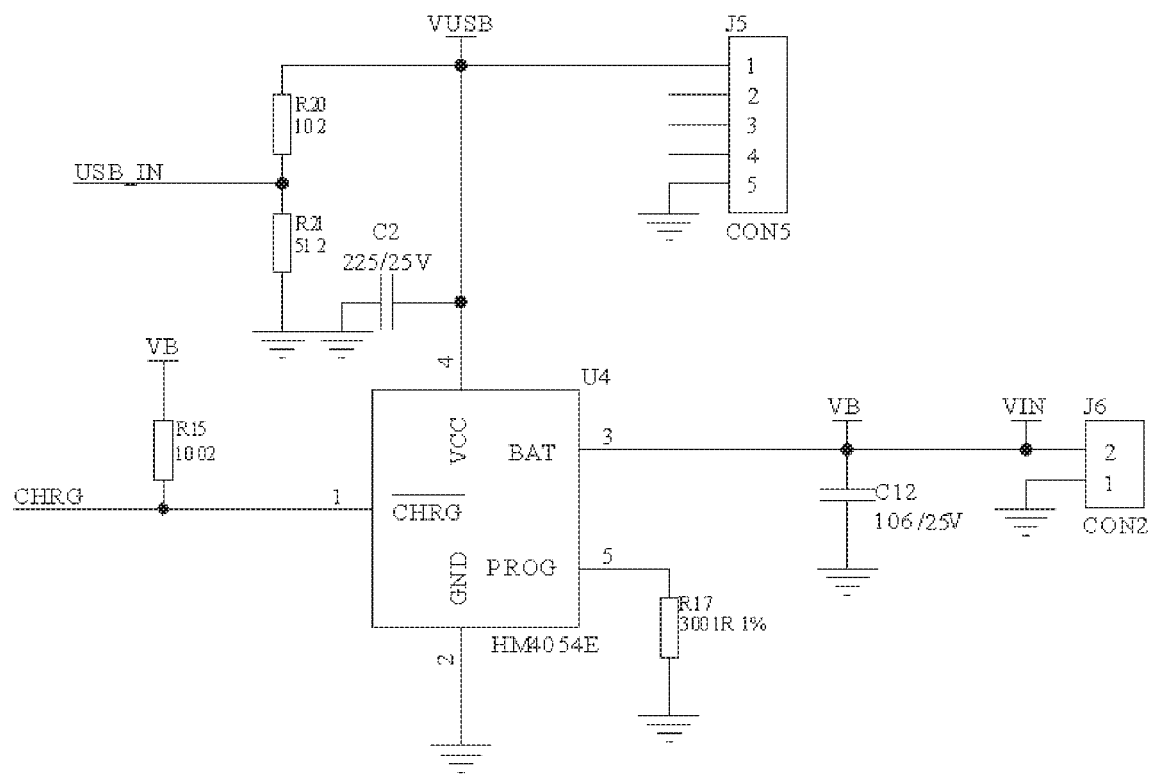
FIG. 19 is a circuit schematic diagram of a charging module in the negative ion generating circuit of the ion pulse treatment apparatus for eye according to the above fourth embodiment of the present invention.

Referring to FIG. 19, the charging module of the power supply unit comprises: a control chip U4, such as HM4054E chip, a pin 1 of the control chip U4 is connected to the booster module through a resistor R15, and the pin 1 of the control chip U4 is also connected to the CPU module, a pin 2 of the control chip U4 is grounded, a pin 3 of the control chip U4 is connected to a connector J6, a pin 2 of the connector J6 is connected to the power input terminal VIN, and the pin 3 of the control chip U4 is connected to a capacitor C12 having another end grounded, and the non-grounded end of the capacitor C12 is connected to the boost module, a pin 4 of the control chip U4 is connected to a capacitor C2 having another end grounded, a pin 4 of the control chip U4 is connected to the VUSB interface circuit, which belongs to the prior art, so that the USB interface is used for charging, the pin 4 of the control chip U4 is also connected to a resistor R20 and a connector J5, the resistor R20 is connected to a resistor R21 having another end grounded, the CPU module is connected between the resistor R20 and the resistor R21.

Figure 20:
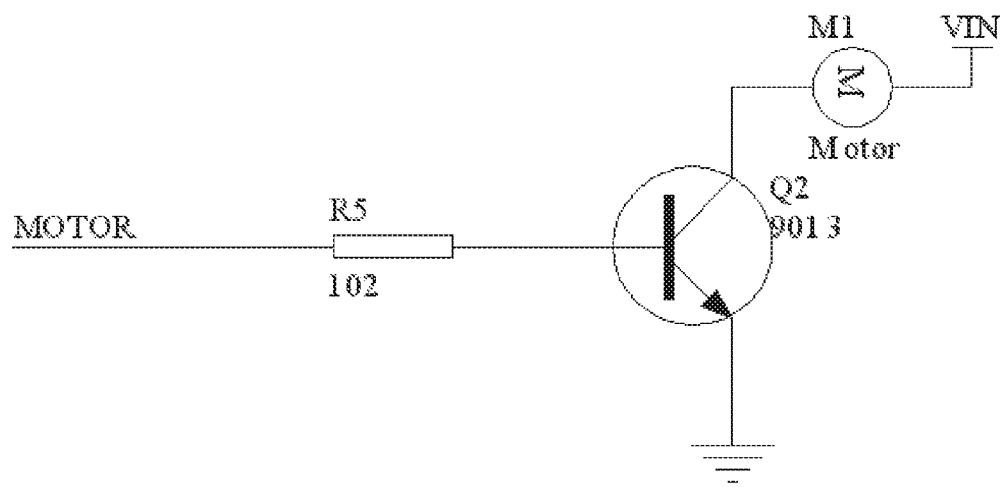
FIG. 20 is a circuit schematic diagram of a vibration motor module in the negative ion generating circuit of the ion pulse treatment apparatus for eye according to the above fourth embodiment of the present invention.

Referring to FIG. 20, the negative ion generating circuit further comprises a vibration motor module connected to the CPU module. The vibration motor module comprises a vibration motor M1, wherein the vibration motor M1 is connected to the power input terminal VIN, wherein the vibration motor M1 is connected to a collector of a transistor Q2, an emitter of the transistor Q2 is grounded, a base of the transistor Q2 is connected to the CPU module through a resistor R5.

Figure 21:
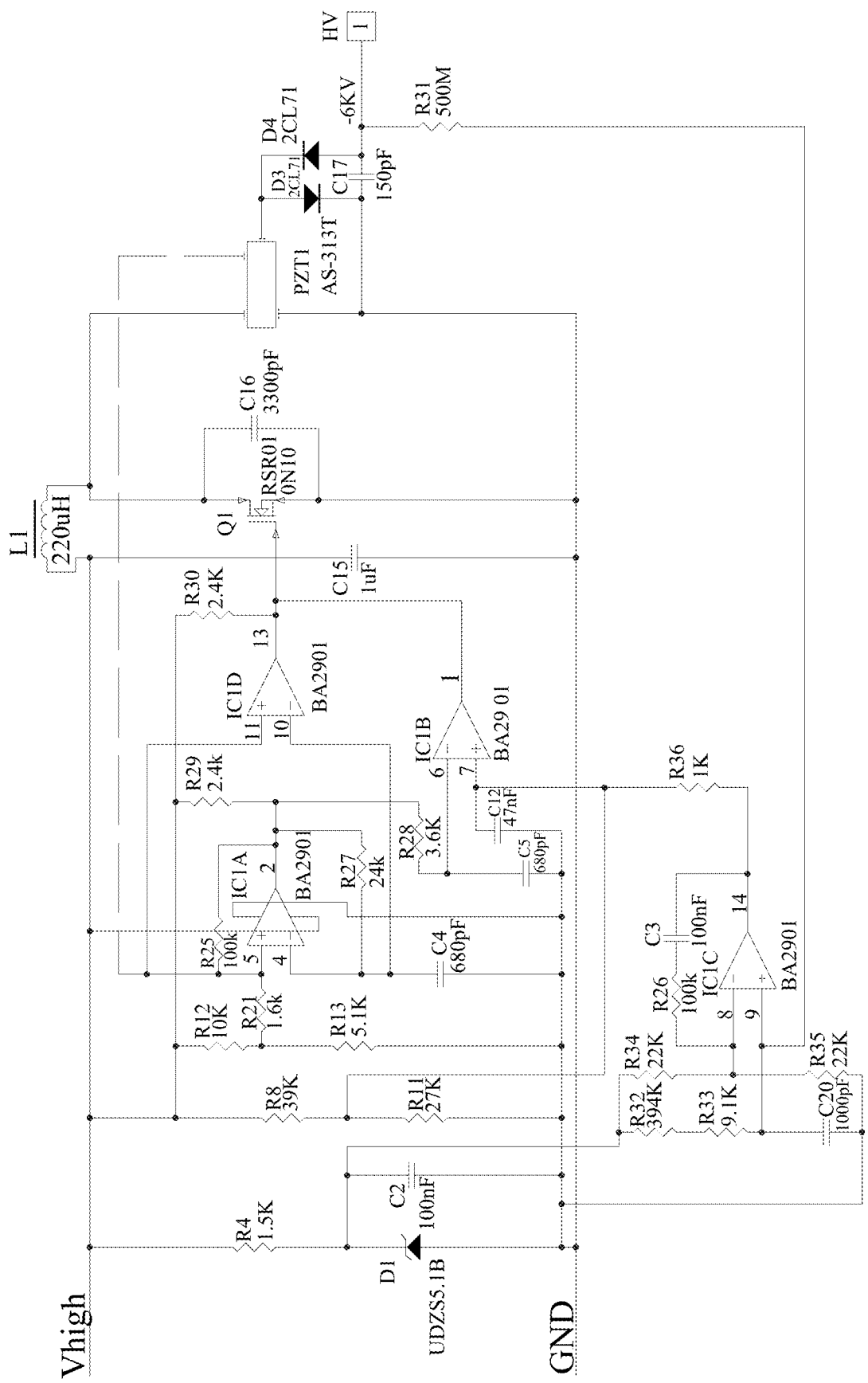
FIG. 21 is a circuit schematic diagram of a high voltage module in the negative ion generating circuit of the ion pulse treatment apparatus for eye according to the above fourth embodiment of the present invention.
Figure 22:
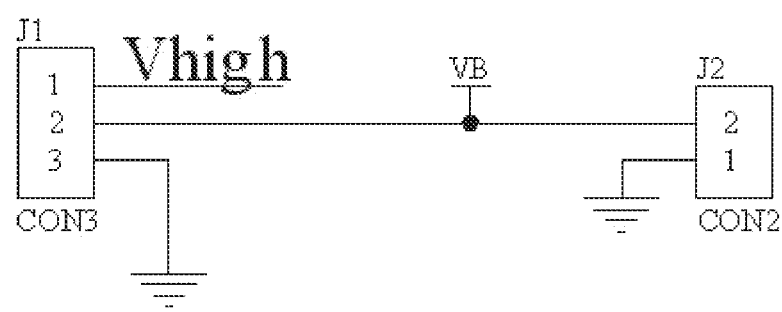
FIG. 22 is a circuit diagram of a connector J1 and a connector J2 in the high voltage module circuit in the negative ion generating circuit of the ion pulse treatment apparatus for eye according to the above fourth embodiment of the present invention.

Referring to FIGS. 21-22, the high voltage module comprises: a voltage comparator IC1B, a voltage comparator IC1C, a voltage comparator IC1D, a transistor Q1, a piezoelectric ceramic transformer PZT1; a connector J1, a connector J2 connected to the charging module of the power supply module; an input voltage terminal of the piezoelectric ceramic transformer PZT1 is connected to a high voltage power supply input terminal of the high voltage plate through an inductor L1, a high voltage power supply input terminal of the inductor L1 is connected with a capacitor C15, and the other end of the capacitor C15 is connected to the ground terminal GND of the high voltage plate, a ground terminal of the piezoelectric ceramic transformer PZT1 is connected to the ground terminal GND of the high voltage plate, an output voltage terminal of the piezoelectric ceramic transformer PZT1 is connected with a diode D3 and a diode D4 which are connected in antiparallel with each other, a capacitor C17 is provided between the diode D3 and the diode D4, the diode D3 and diode D4 connected in antiparallel with each other are connected to the high voltage output terminal HV; the S pole of a transistor Q1 is connected to the connection end of the inductor L1, which is connected with the piezoelectric ceramic transformer PZT1, the D pole of the transistor Q1 is connected to the ground terminal GND of the high voltage plate, the G pole of the transistor Q1 is connected to the output terminals of the voltage comparator IC1D and the voltage comparator IC1B, a capacitor C16 is connected between the S and D poles of the transistor Q1; the non-inverting input terminal of the voltage comparator IC1D is connected to the non-inverting input terminal of the voltage comparator IC1A, and the inverting input terminal of the voltage comparator IC1D is connected to the inverting input terminal of the voltage comparator IC1A; the inverting input terminal of the voltage comparator IC1B is connected to the output terminal of the voltage comparator IC1A through a resistor R28, the non-inverting input terminal of the voltage comparator IC1B is connected to the ground terminal GND of the high voltage plate through the capacitor C12, a capacitor C5 is connected between the ground terminal of the capacitor C12 and the inverting input terminal of the voltage comparator IC1B; the non-inverting input terminal of the voltage comparator IC1A is connected to the resistor R21, the inverting input terminal of the voltage comparator IC1A is connected to the ground terminal GND of the high voltage plate through a capacitor C4, a resistor R25 is connected between the non-inverting input terminal and the output terminal of the voltage comparator IC1A, the VCC terminal of the voltage comparator IC1A is connected to a pin 1 of the connector J1, the ground terminal of the voltage comparator IC1A is connected to the ground terminal GND of the high voltage plate, a resistor R4 and a diode D1 are provided between the high voltage power input terminal of the high voltage plate and the ground terminal GND of the high voltage plate, the diode D1 is connected in parallel with a capacitor C2, a resistor R8 and a resistor R11 are provided between the high voltage power supply input terminal of the high voltage plate and the ground terminal GND of the high voltage plate, the high voltage power input terminal of the resistor R8 is connected to the resistor R12, the resistor R29, and the resistor R30, the resistor R12 is connected to the resistor R21 and the resistor R13, the resistor R13 is connected to the ground terminal GND of the high voltage plate, a resistor R27 is connected between the inverting input terminal and the output terminal of the voltage comparator IC1A; the output terminal of the voltage comparator IC1C is connected to the non-inverting input terminal of the voltage comparator IC1B and between the resistor R8 and the resistor R11 through a resistor R36, a resistor R26 and a capacitor C3 are connected in series between the inverting input terminal and the output terminal of the voltage comparator IC1C, the inverting input terminal of the voltage comparator IC1C is connected to the resistor R34 and the resistor R35, the non-inverting input terminal of the voltage comparator IC1C is connected to the resistor R33 and the capacitor C20, the resistor R34 and the resistor R32 are connected between the capacitor C2, the resistor R4 and the diode D1, the capacitor C20 and resistor R35 are connected to the ground terminal GND of the high voltage plate, the non-inverting input terminal of the voltage comparator IC1C is connected to the high voltage output terminal HV through a resistor R31.

When the two electrodes are connected to the negative ion generating circuit, one electrode is connected to the high voltage output terminal HV of the high voltage module, and the other electrode is grounded, here, the high voltage module is arranged as an independent module, for example, a circuit board is arranged separately (that is, the high voltage generating element 15 mentioned in embodiment 1 in FIG. 12), while the CPU module (and peripheral circuits), the boost module, the power supply unit and the vibration motor module are integrated on a PCB circuit board (that is, the control board 16 mentioned in embodiment 1 in FIG. 12, the power supply 14 can be integrated into the control board 16 or arranged separately at this time), at this time, the motor that needs to be grounded is directly connected to the ground terminal of the PCB circuit board.

Those skilled in the art should appreciate that the aforementioned embodiments are specific embodiments for implementing the present disclosure. In practice, however, various changes may be made in the forms and details of the specific embodiments without departing from the spirit and scope of the present disclosure.

What is claimed is:

1. An ion pulse treatment apparatus for eye, comprising:
   two conductor elements;
   a carrier for carrying said conductor elements to two Jingming acupoints respectively;
   a high voltage generating element provided at said carrier, wherein one conductor element is electrically connected to a ground terminal of said high voltage generating element, and the other conductor element is electrically connected to a high voltage output terminal of said high voltage generating element;
   a power supply provided at said carrier; and
   a control board, wherein said power supply and said high voltage generating element are respectively and electrically connected to said control board, wherein said carrier is a spectacle frame, wherein said spectacle frame comprises two spectacle temples, two spectacle rings, a nose bridge and two nose pads, wherein said spectacle rings are connected with each other by said nose bridge, wherein said conductive elements define said nose pads respectively, wherein said conductive elements are made of conductive materials and integrated on said spectacle rings respectively, wherein each of said conductive elements is configured to be a disc-shaped metal conductor to provide a surface contact to a skin surface corresponded to a Jingming acupoint, wherein said control board comprises a CPU module, a booster module, a high voltage module and a power supply unit, wherein said power supply unit comprises a charging module, a charger and a battery, wherein said charging module is electrically connected with said battery and said charger respectively, wherein said booster module is electrically connected with said high voltage generating element, wherein a control chip of said CPU module is electrically connected with said booster module through at least one pin, said booster module is connected to said high voltage module and said control chip of said CPU module is electrically connected with said charging module through at least two pins, wherein another pin of said control chip of said CPU module is respectively connected with at least three capacitors, and at least two of said three capacitors are respectively and electrically connected with said power supply through a same resistance, wherein said high voltage module comprises a voltage comparator IC1B, a voltage comparator IC1C, a voltage comparator IC1D, a transistor Q1, a piezoelectric ceramic transformer PZT1, wherein said piezoelectric ceramic transformer PZT1 has an input voltage terminal connected to a high voltage power supply input terminal of a high voltage plate through an inductor L1, a ground terminal connected to a ground terminal GND of said high voltage plate and an output voltage terminal connected with a diode D3 and a diode D4, wherein said transistor Q1 has a S pole connected to an inductor L1, a D pole connected to said ground terminal GND of said high voltage plate and a G pole connected to an output terminal of said voltage comparator IC1D and a capacitor C16 is connected between said S pole and said D pole, wherein a non-inverting input terminal of said voltage comparator IC1D is connected to a non-inverting input terminal of said voltage comparator IC1A, and an inverting input terminal of said voltage comparator IC1D is connected to an inverting input terminal of said voltage comparator IC1A, wherein said inverting input terminal of said voltage comparator IC1B is connected to an output terminal of said voltage comparator IC1A through a resistor R28, said non-inverting input terminal of said voltage comparator IC1B is connected to said ground terminal GND of said high voltage plate through a capacitor C12, a capacitor C5 is connected between said ground terminal of said capacitor C12 and said inverting input terminal of said voltage comparator IC1B, wherein said non-inverting input terminal of said voltage comparator IC1A is connected to a resistor R21, wherein said voltage comparator IC1C has an output terminal connected to said non-inverting input terminal of said voltage comparator IC1B and between a resistor R8 and a resistor R11 through a resistor R36 and an inverting input terminal connected to a resistor R34 and a resistor R35, said non-inverting input terminal of said voltage comparator IC1C is connected to said resistor R33 and said capacitor C20.

2. The ion pulse treatment apparatus for eye, as recited in claim 1, wherein said spectacle frame defines a concealed wiring groove, wherein said power supply, said high voltage generating element and said control board are provided within said concealed wiring groove.

3. The ion pulse treatment apparatus for eye, as recited in claim 2, wherein said concealed wiring groove defines two circumferential grooves surrounding said spectacle rings respectively and a nose bridge groove communicated with said circumferential grooves respectively.

4. The ion pulse treatment apparatus for eye, as recited in claim 1, further comprising two counterweights, wherein each of said two spectacle temples of said spectacle frame comprises an ear front portion, an ear rear portion and an ear support portion, wherein said ear support portion is provided between said ear front portion and said ear rear portion, wherein said counterweights are respectively provided at said ear rear portion of said spectacle temples.

5. The ion pulse treatment apparatus for eye, as recited in claim 1, further comprising a vibration motor module, wherein said vibration motor module comprises a vibration motor and a triode, wherein said vibration motor is respectively and electrically connected with a collector of said triode and said power supply, the emitter of said triode is grounded, and the base of said triode is electrically connected with said CPU module through at least one resistor.

6. The ion pulse treatment apparatus for eye, as recited in claim 4, wherein two batteries of said power supply define said counterweights respectively.

7. The ion pulse treatment apparatus for eye, as recited in claim 1, wherein said nose pad comprises a nose arm and a supporting leaf installed with said nose arm, wherein said nose arm and said supporting leaf are made of conductive material.

* * * * *